US011649723B2

(12) United States Patent
Allo

(10) Patent No.: US 11,649,723 B2
(45) Date of Patent: May 16, 2023

(54) METHOD AND SYSTEM FOR ESTIMATING IN-SITU POROSITY USING MACHINE LEARNING APPLIED TO CUTTING ANALYSIS

(71) Applicant: CGG SERVICES SAS, Massy (FR)

(72) Inventor: Fabien Allo, Calgary (CA)

(73) Assignee: CGG SERVICES SAS, Massy (FR)

( * ) Notice: Subject to any disclaimer, the term of this patent is extended or adjusted under 35 U.S.C. 154(b) by 575 days.

(21) Appl. No.: 16/393,449

(22) Filed: Apr. 24, 2019

(65) Prior Publication Data

US 2020/0340907 A1 Oct. 29, 2020

(51) Int. Cl.
| | |
|---|---|
| *E21B 49/00* | (2006.01) |
| *G01N 15/08* | (2006.01) |
| *G06T 7/00* | (2017.01) |
| *G06F 18/214* | (2023.01) |
| *G06F 18/21* | (2023.01) |
| *G06F 18/2431* | (2023.01) |

(Continued)

(52) U.S. Cl.
CPC ....... *E21B 49/005* (2013.01); *G01N 15/0806* (2013.01); *G01N 15/088* (2013.01); *G06F 18/214* (2023.01); *G06F 18/217* (2023.01); *G06F 18/2431* (2023.01); *G06T 7/001* (2013.01); *G06V 10/454* (2022.01); *G06V 10/764* (2022.01); *G06V 10/82* (2022.01); G06T 2207/10061 (2013.01); G06T 2207/20081 (2013.01); G06T 2207/30181 (2013.01)

(58) Field of Classification Search
CPC ...... G01N 15/088; G01N 15/00; G01N 15/08; G01N 15/0806; G01N 2015/0833; G06K 9/6256; G06K 9/6257; G06K 9/6262; G06K 9/628; G06T 7/001; G06T 2207/20081; G06T 2207/20084; G06T 2207/20092; G06T 2207/3018
USPC ........................................................ 382/109
See application file for complete search history.

(56) References Cited

U.S. PATENT DOCUMENTS

| | | | |
|---|---|---|---|
| 7,500,388 B2 * | 3/2009 | Fujisawa | ................. E21B 49/06 73/152.11 |
| 8,249,363 B2 | 8/2012 | Lee et al. | |

(Continued)

FOREIGN PATENT DOCUMENTS

WO 2018047009 A1 3/2018

OTHER PUBLICATIONS

A.Y. Bukharev et al., "Automatic Analysis Of Petrographic Thin Section Images Of Sandstone", 16th European Conference on the Mathematics of Oil Recovery, Sep. 3-6, 2018, Barcelona, Spain.

(Continued)

*Primary Examiner* — Huy C Ho
(74) *Attorney, Agent, or Firm* — Patent Portfolio Builders PLLC

(57) ABSTRACT

A method for estimating in-situ porosity based on cutting images employs a neural network trained with labeled images, the labels indicating wireline porosity values. The method may be used to obtain porosity values along a vertical, deviated or horizontal well, where wireline logging data is not available or unreliable. The method uses machine learning. Training and validating the neural network may be ongoing processes in the sense that any new labeled image that becomes available can be added to the training set and the neural network being retrained to enhance its predictive performance.

20 Claims, 8 Drawing Sheets

(51) Int. Cl.
*G06V 10/764* (2022.01)
*G06V 10/82* (2022.01)
*G06V 10/44* (2022.01)

(56) References Cited

U.S. PATENT DOCUMENTS

| | | | | |
|---|---|---|---|---|
| 8,583,410 | B2* | 11/2013 | Sisk | G01N 33/24 |
| | | | | 703/10 |
| 8,731,889 | B2* | 5/2014 | Du | E21B 43/267 |
| | | | | 703/10 |
| 9,613,253 | B2* | 4/2017 | Ly | H05K 999/99 |
| 2005/0206890 | A1* | 9/2005 | Hurst | G06T 7/0002 |
| | | | | 356/239.7 |
| 2008/0219495 | A1 | 9/2008 | Hulten et al. | |
| 2010/0131204 | A1* | 5/2010 | Dvorkin | G01V 1/30 |
| | | | | 702/6 |
| 2011/0004448 | A1* | 1/2011 | Hurley | G06T 17/00 |
| | | | | 703/1 |
| 2013/0259190 | A1* | 10/2013 | Walls | G01N 33/24 |
| | | | | 378/9 |
| 2013/0301794 | A1* | 11/2013 | Grader | G01N 23/087 |
| | | | | 378/5 |
| 2014/0361466 | A1* | 12/2014 | Kimour | G01N 1/36 |
| | | | | 264/496 |
| 2017/0023689 | A1 | 1/2017 | Spence et al. | |

OTHER PUBLICATIONS

Leena Lepisto et al., "Comparison of some content-based image retrieval systems with rock texture images", pp. 1-8.

Salaheldin Elkatatny et al., "New insights into porosity determination using artificial intelligence techniques for carbonate reservoirs", Petroleum, Apr. 9, 2018, pp. 1-11.

Al-Mudhafar, W.J., "Integrating well log interpretations for lithofacies classification and permeability modeling through advanced machine learning algorithms," Journal of Petroleum Exploration and Production Technology, vol. 7, No. 4, 2017 (Published online Jun. 13, 2017), pp. 1023-1033.

Extended European Search Report, dated Sep. 18, 2020, for European Application No. 20315053.7 (Note that document D3 in this Extended European Search Report—that is, "New insights into porosity determination using artificial intelligence techniques for carbonate reservoirs" by Elkatatny et al.—was cited in the IDS filed Apr. 24, 2019).

Hamada, G.M., et al., "Neural network prediction of porosity and permeability of heterogeneous gas sand reservoirs using NMR and conventional logs," NAFTA, vol. 61, No. 10, Jan. 1, 2010, pp. 451-460.

Karimpouli, S., et al., "Image-based velocity estimation of rock using Convolutional Neural Networks," Neural Networks, vol. 111, Mar. 2019 (Available online Jan. 9, 2019), pp. 89-97.

Singh, S., et al., "A general approach for porosity estimation using artificial neural network method: a case study from Kansas gas field," Studia Geophysica et Geodaetica, vol. 60, No. 1, 2016 (Published Nov. 14, 2015), pp. 130-140.

Valentín, M.B., et al., "A deep residual convolutional neural network for automatic lithological facies identification in Brazilian pre-salt oilfield wellbore image logs," Journal of Petroleum Science and Engineering, vol. 179, Aug. 2019 (Available online Apr. 19, 2019), pp. 474-503.

Examination Report in corresponding/related EP Application No. 20 315 053.7 dated Sep. 5, 2022.

Manuel Blanco Valentin et al., "Estimation of permeability and effective porosity logs using deep autoencoders in borehole image logs from the brazilian pre-salt carbonate," Journal of Petroleum Science and Engineering, 2018, vol. 170, pp. 315-330.

* cited by examiner

FIGURE 5

| Class Porosity | 0% | 1% | 2% | 3% | 4% | 5% | 6% | 7% | 8% | 9% | 10% |
|---|---|---|---|---|---|---|---|---|---|---|---|
| Estimated porosity (from most likely to less likely) | 0% (0.46) | 1% (0.44) | 2% (0.46) | 3% (0.73) | 4% (0.17) | 2% (0.24) | 3% (0.08) | 6% (0.74) | 6% (0.41) | 8% (0.34) | 10% (0.35) |
| | 1% (0.44) | 0% (0.23) | 3% (0.25) | 6% (0.10) | 5% (0.11) | 5% (0.29) | 6% (0.63) | 7% (0.09) | 6% (0.22) | 6% (0.29) | 10% (0.25) |
| | 3% (0.04) | 3% (0.11) | 1% (0.15) | 2% (0.05) | 4% (0.11) | 3% (0.10) | 7% (0.07) | 5% (0.10) | 5% (0.21) | 7% (0.10) | 6% (0.10) |
| | 4% (0.02) | 2% (0.10) | 4% (0.07) | 8% (0.09) | 2% (0.10) | 1% (0.13) | 4% (0.05) | 6% (0.04) | 4% (0.08) | 5% (0.03) | 4% (0.03) |
| | 6% (0.02) | 4% (0.01) | 0% (0.03) | 7% (0.02) | 3% (0.02) | 7% (0.04) | 9% (0.05) | 3% (0.02) | 3% (0.00) | 10% (0.03) | 3% (0.04) |

FIGURE 6

| True Porosity | 0% | 1% | 2% | 2% | 3% |
|---|---|---|---|---|---|
| Estimated porosity (from most likely to less likely) | 7% (0.40) | 3% (0.32) | 7% (0.51) | 7% (0.84) | 7% (0.47) |
| | 2% (0.22) | 2% (0.21) | 6% (0.18) | 2% (0.05) | 6% (0.34) |
| | 5% (0.10) | 1% (0.13) | 3% (0.09) | 5% (0.04) | 8% (0.08) |
| | 4% (0.08) | 5% (0.13) | 8% (0.07) | 0% (0.02) | 3% (0.04) |
| | 3% (0.07) | 6% (0.07) | 2% (0.05) | 6% (0.02) | 2% (0.02) |

METHOD AND SYSTEM FOR ESTIMATING IN-SITU POROSITY USING MACHINE LEARNING APPLIED TO CUTTING ANALYSIS

BACKGROUND

Technical Field

Embodiments of the subject matter disclosed herein generally relate to methods and systems for estimating in-situ porosity (i.e., in an explored subsurface formation) based on cutting analysis and using machine learning techniques.

Discussion of the Background

In an explored subsurface formation, porosity is a significant piece of information for predicting the formation's elastic (e.g., bulk density, compressional and shear wave velocity) and mechanical (e.g., Young modulus, Poisson ratio) properties. Even a relatively small uncertainty in the porosity value causes large uncertainties in the predicted elastic and mechanical properties. Cuttings are readily available as a byproduct of the drilling process and their porosity can be measured. U.S. Pat. No. 9,613,253, which is incorporated herein by reference in its entirety, describes the use of scanning electron microscope (SEM) for cutting analysis. U.S. Patent Application Publication No. 2017/0023689 (which is also incorporated herein by reference in its entirety) describes a workflow for evaluating elastic and mechanical properties based on cutting analysis as an alternative to wireline logging data.

Cutting porosity differs from in-situ porosity (i.e., porosity of the rock at the location from which the cutting was removed), making it challenging to predict in-situ rock properties. Several factors contribute to this difference. The drilling process breaks the rock and therefore alters the porosity of the cuttings due to cracks and fractures that did not exist in-situ. The decrease of the pressure from the in-situ conditions to the surface causes an increase of porosity (as pressure on the pores decreases). The temperature may also be significantly different at the surface than in-situ causing porosity changes (in clay minerals for example). Actual in-situ porosity may be lower than the cutting porosity because the rock preferentially breaks along the pores, which have less resistance than the rock frame made of minerals.

Porosity values from wireline logging data are closer to in-situ porosity values, but wireline logging is rarely used in non-vertical wells due to high costs and risk of losing the well if the tool gets stuck. FIG. 1 is a graph illustrating the difference between log porosity (the continuous line) and cutting porosity (the dashed line connecting small circles) estimated using image processing. The differences may exceed 50 percent (half of the wireline porosity value).

As of now, the best measure of in-situ porosity is obtained using cores. Unlike the cuttings that are a byproduct of drilling, cores are purposefully carved-out pieces of rock. Core porosity may be measured more thoroughly, for example, measuring pores' volume by saturating the core with a liquid and computing the ratio of the liquid volume to the core volume. Given the time and effort required to cut and bring to the surface such cores, they are infrequently sampled along wells. The larger circles in FIG. 1 indicate some core porosity values.

Elastic and mechanical properties along wellbores are used for appraising hydrocarbon potential and optimizing stage placement for hydraulic stimulation in unconventional oil and gas reservoirs (i.e., reservoirs from which oil and gas are recovered using fracking). PCT publication WO 2018/047009, which is also incorporated herein by reference in its entirety, discloses a workflow for the use of geologic indicators obtained from cutting analysis for designing simulation operations.

There is a need to develop methods for faster and cheaper estimation of in-situ porosity values using cutting analysis.

SUMMARY

Various embodiments use machine learning to estimate porosity in wells based on cutting images. Training images labeled with wireline porosity values are used to train a neural network. The trained neural network is then used to estimate in-situ porosity values based on cutting images.

According to an embodiment, there is a method for estimating in-situ porosity based on cutting images. The method includes obtaining an image of cuttings associated with a location along a well in a subsurface rock formation and estimating an in-situ porosity value for the location based on the image using a neural network trained with labeled images. Here, labels of the labeled images indicate porosity values. The in-situ porosity value is usable to infer elastic and/or mechanical properties at the location.

According to another embodiment there is a system for estimating in-situ porosity based on cutting images including a data processing apparatus with an interface and a central processing unit. The interface is configured to receive an image of cuttings associated with a location along a well in a subsurface rock formation. The central processing unit is connected to the interface and is configured to estimate an in-situ porosity value for the location based on the image using a neural network trained with labeled images. Labels of the labeled images indicate porosity values and the in-situ porosity value is usable to infer elastic and/or mechanical properties at the location.

According to yet another embodiment there is a computer readable recording media storing executable codes, which, when executed by a processor connected to an interface, make the processor to estimate an in-situ porosity value for a location along a well in a subsurface rock formation based on a cutting image received by the interface, using a neural network. This neutral network has been trained with labeled images, where labels of the labeled images indicate known porosity values.

BRIEF DESCRIPTION OF THE DRAWINGS

For a more complete understanding of the present inventive concept, reference is now made to the following descriptions taken in conjunction with the accompanying drawings, in which:

FIG. 5 is a table illustrating validation with a random subset of labeled images;

FIG. 6 is a table illustrating a blind test;

DETAILED DESCRIPTION OF THE INVENTION

The following description of the exemplary embodiments refers to the accompanying drawings. The same reference numbers in different drawings identify the same or similar elements. The following detailed description does not limit the invention. Instead, the scope of the invention is defined by the appended claims. The following embodiments are discussed using the terminology of geological analysis and fracking operations.

Reference throughout the specification to "one embodiment" or "an embodiment" means that a particular feature, structure or characteristic described in connection with an embodiment is included in at least one embodiment of the subject matter disclosed. Thus, the appearance of the phrases "in one embodiment" or "in an embodiment" in various places throughout the specification is not necessarily referring to the same embodiment. Further, the particular features, structures or characteristics may be combined in any suitable manner in one or more embodiments.

Various embodiments described in this section provide estimates of in-situ porosity values based on cutting images. The embodiments are trained using labeled cutting images and wireline porosity values acquired using a wireline logging tool. Machine learning techniques are used to link wireline porosity values to cutting images, yielding a better estimate of in-situ porosity based on the cutting images only.

Figure 1:
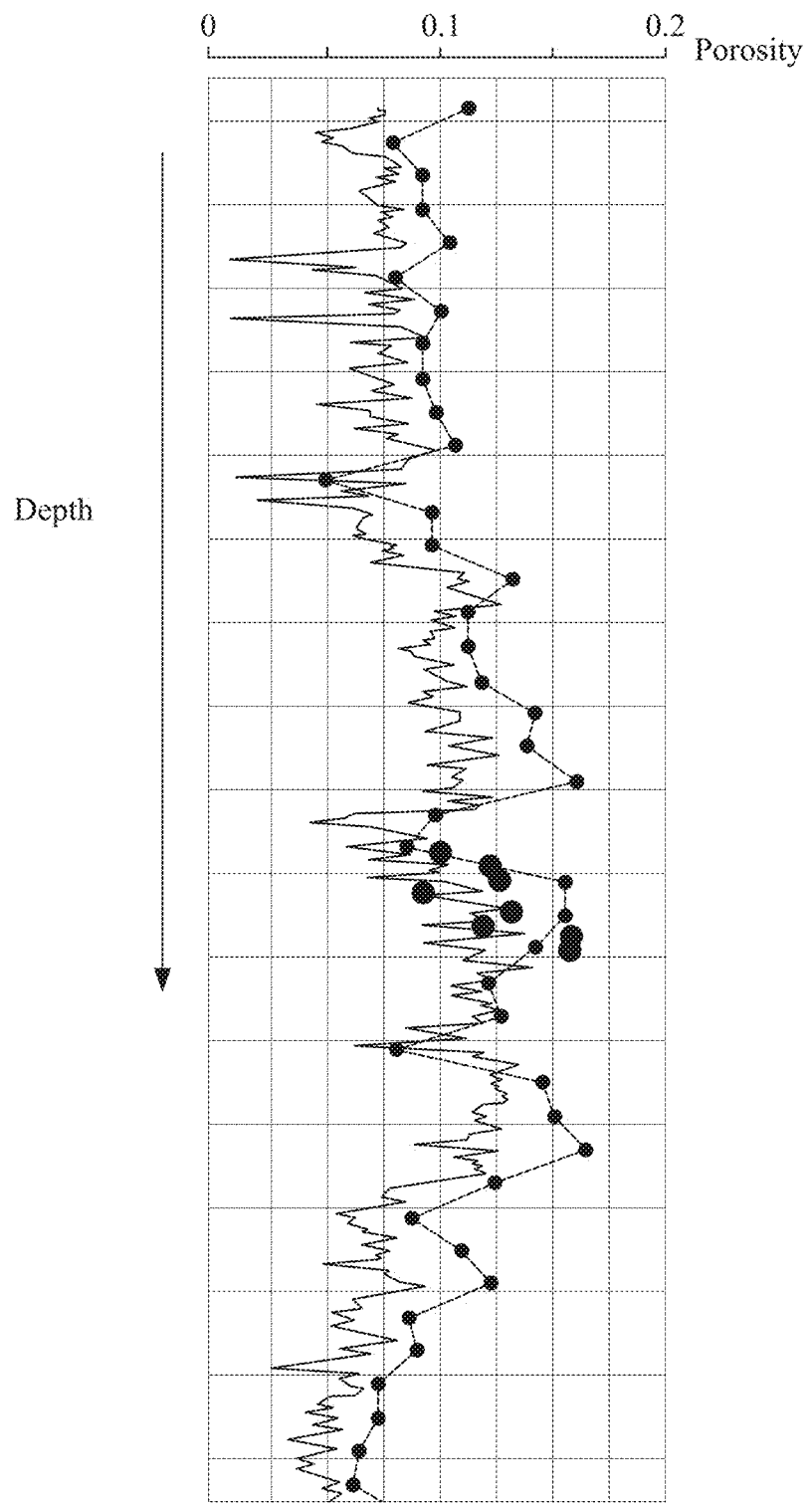
FIG. 1 is a graph illustrating different porosity measurements.
Figure 2:
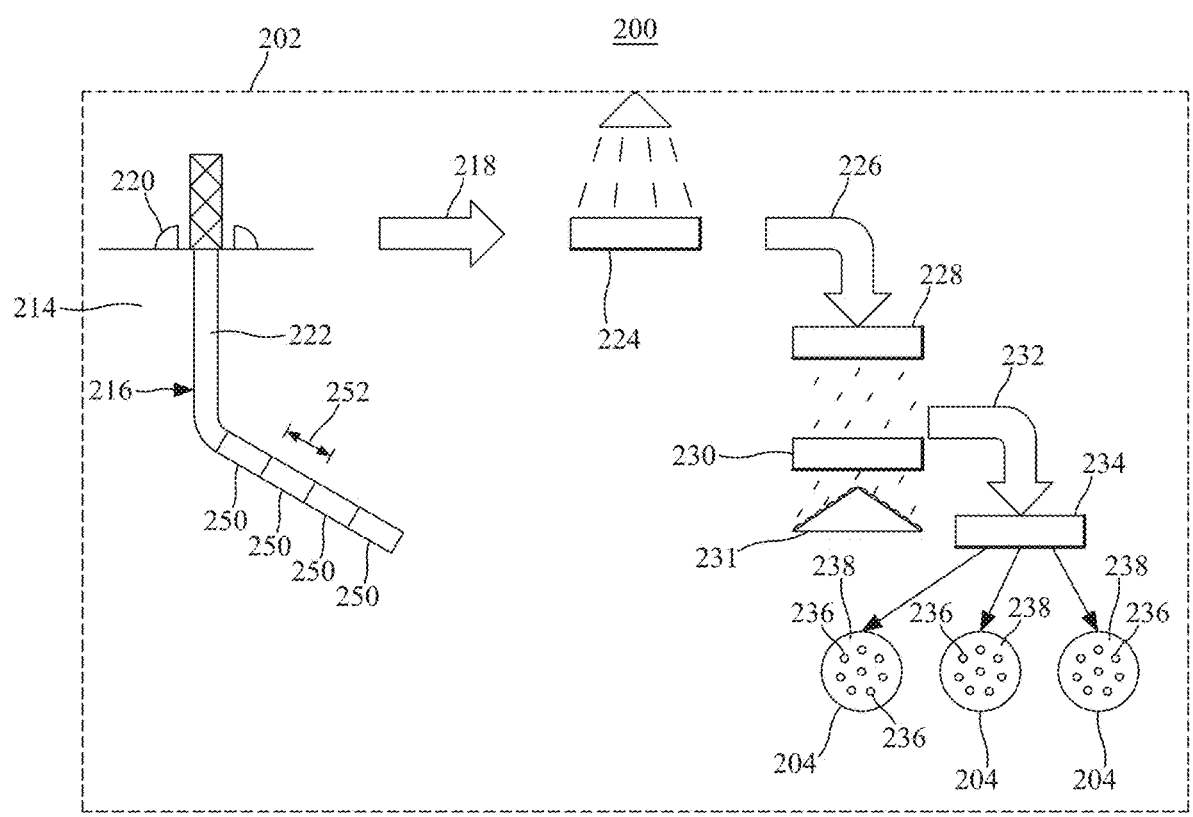
FIG. 2 is an illustration of cutting preparation for SEM analysis.

As illustrated in FIG. 2, cuttings are collected from locations 250 along a well 216 drilled in a subsurface formation 214, for example, within an interval 252 of about 30 ft. While 30 feet is the standard interval between collection of cuttings, but the cuttings might not represent the full interval. Sometimes, the operator fills a bag at regular time intervals which, based on the drilling speed, corresponds to a given depth interval (e.g., the standard is 30 feet). Collecting cuttings more often (e.g., a 10 ft interval) is possible but more expensive.

The well may have a vertical portion 222 and a non-vertical portion 223 (which may even be horizontal). Although the locations 250 are illustrated along the non-vertical portion, this is merely an illustration and not a limitation.

Geological material (including the cuttings) obtained during drilling is ejected at the surface (see piles 220) using either water-based or an oil-based mud. The geological material 218 may then be processed to select suitable cuttings in the following exemplary manner. In a washing station 224, petrochemical fluids and water, as well as other organic and inorganic solvents and detergents, are first used to produce cleaned geological material 226. Washing stations and methods for cleaning the geological material are known in the art.

The cleaned geological material 226 (which includes the cuttings) is then passed through a coarse sieve 228 to remove all material equal to or greater than 2 mm in size, which can be referred to as cave-in material. The material of less than 2 mm in size is further passed through a finer sieve 230 that allows fine rock flour 231 to pass there-through if its size is less than about 0.06 mm (60 μm).

The remaining cleaned and sieved geological material 232, which is smaller than cave-in and larger than rock flour (i.e., contains particles in from about 0.06 mm to about 2 mm), is passed through a sample preparation system 234 to be prepared for analysis. The sample preparation system immobilizes the particles 236 in a polymerized plastic or resin block 238 and exposes a cross-sectional surface of one plane of the block. This exposes a cross-section of multiple geological particles 236.

The sample including cuttings thus prepared may be analyzed with a Scanning Electron Microscope (SEM) with Energy Dispersive X-Ray (EDX) system (e.g., RoqScan™ technology). The analysis yields high-resolution images usable for estimating mineral volumes, macro-porosity, grain size, pore size, grain geometry, pore and grain aspect ratios and number of weakness planes, etc.

Figure 3:
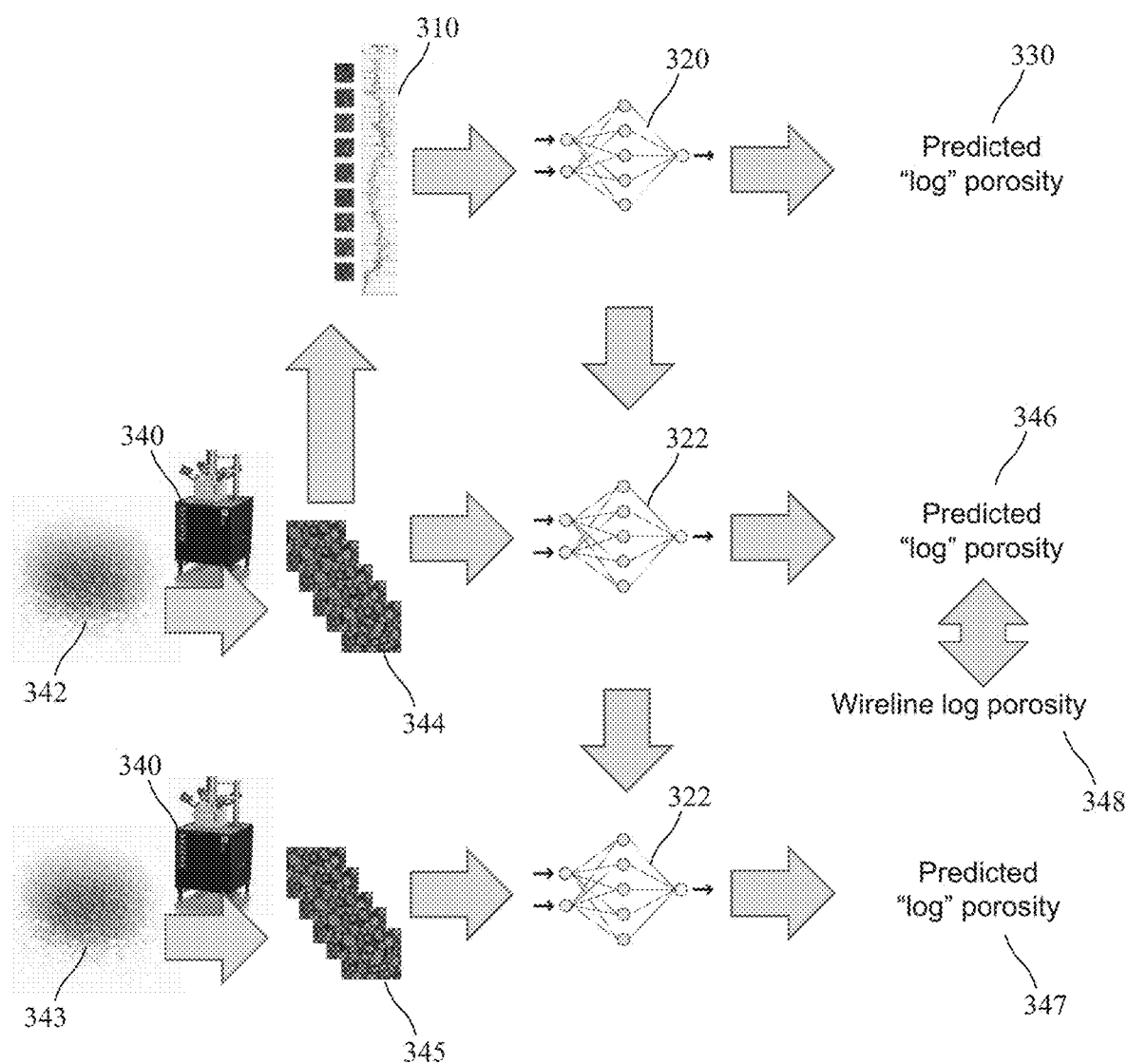
FIG. 3 illustrates a workflow according to an embodiment.

FIG. 3 is a workflow illustrating the machine learning approach used in the following embodiments. A first phase is a supervised training of a neural network (NN) 320 using existing datasets 310 made of labeled cutting images. NN is a term used to indicate a set of algorithms designed to recognize patterns by labeling and clustering raw input. An example of image recognition/comparison software is IBM's Query by Image Content package (QBIC™), but many others are known and publicly available.

Figure 4:
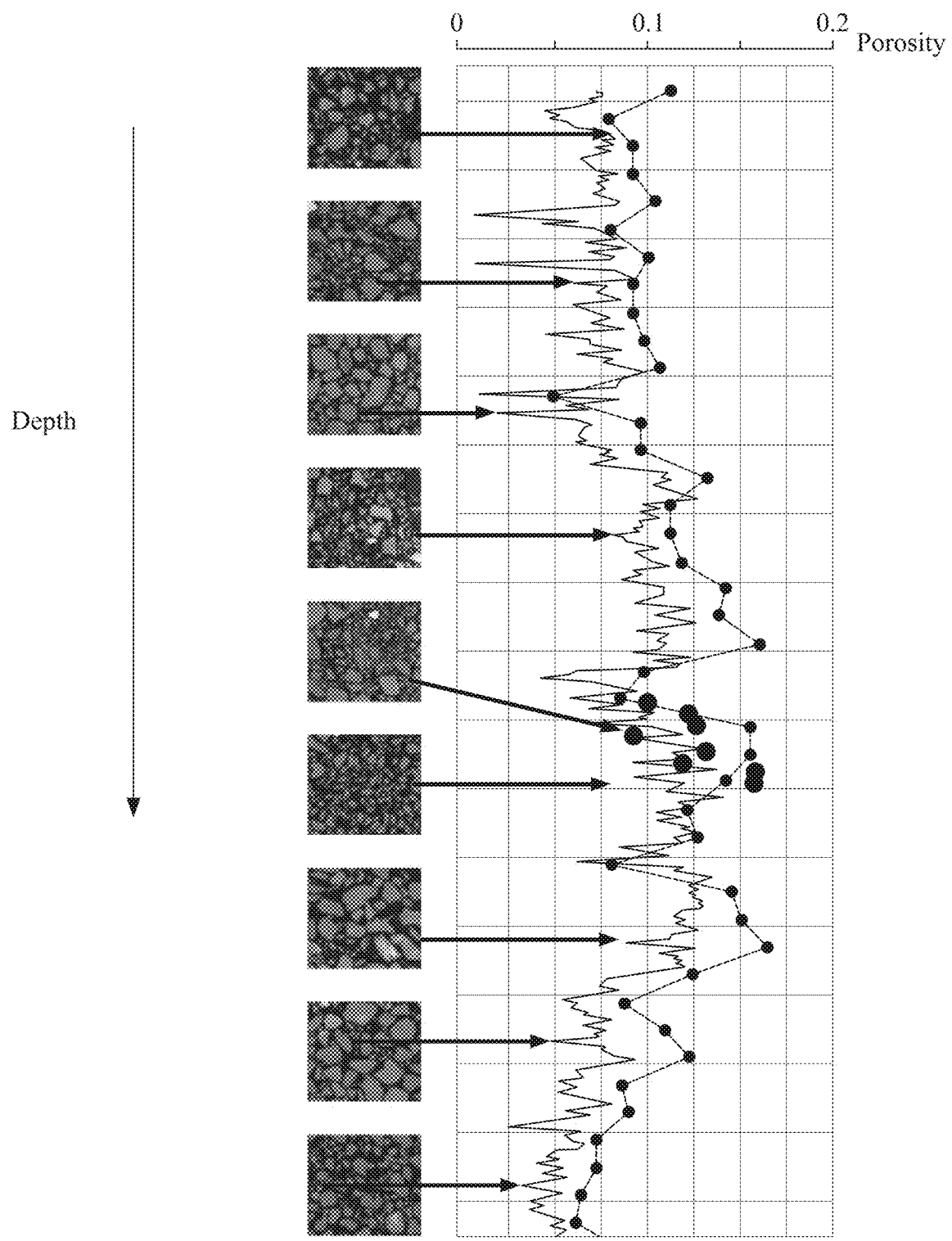
FIG. 4 illustrates correspondence between images and porosity values.

FIG. 4 illustrates cuttings images (on the left column) labeled with wireline porosity values used to train the NN. The porosity value associated with each image may be an average wireline porosity value calculated using porosity values (often acquired as frequent as every half ft) for a length similar to the cutting sampling interval (e.g., 30 ft). Training makes the NN able to determine porosity values 330 (named "predicted log values" to suggest that they look like a log although they were not obtained using a logging tool) for images similar to the labeled images in the training dataset 310.

A second (optional) phase is validation using cutting images and wireline logging data of selected vertical wells. Cuttings 342 are prepared and analyzed with a SEM 340 to obtain unlabeled images 344. These images are input to the trained neural network 322, which then outputs predicted "log" porosity values 346. These values are then compared with corresponding (i.e., for the same locations along the well) wireline porosity values 348. If the predicted porosity is close to the measured one, the NN was trained appropriately to characterize that particular cutting sample. If not, the training set used to train the NN was not representative of the particular cutting sample and the NN therefore couldn't predict accurately its porosity. In both cases, the sample and the corresponding measured porosity may be added to the training set to retrain the NN to improve and extend its porosity estimate ability.

The table in FIG. 5 illustrates results of a validation process. While a training data set is used to adjust weights in the neural network, a validation data set is used to minimize overfitting. The weights of the network are not adjusted using the validation dataset, instead the validation dataset being used to verify that any increase in accuracy over the training data set actually yields an increase in accuracy over a dataset that has not been shown to the network before, or at least the network hasn't trained on it (i.e., the validation data set). If the accuracy over the training data set increases, but the accuracy over the validation data set stays the same or decreases, the neural network is overfitted and training should be stopped.

A testing dataset may then be used for assessing the NN's actual predictive power (i.e., a blind test). The validation process may be performed automatically by the software that provides the NN capability. In this case, the user doesn't split the images between the training set and validation set it is done automatically and randomly. Whether validation is performed may not be user's option as it lowers likelihood of overfitting the data. The blind test on the other hand is optional triggers by a user in most cases. FIG. 6 illustrate a blind test result in the same presentation manner as FIG. 5.

As already mentioned, the cutting images used in the validation process are different from the labeled images used for training. However, the validation images are associated with some porosity values (classes) listed in the first line of the table. Each column gives the result of the classification done for a particular sample. The first line indicates the true porosity (so the target). The five following cells of a row gives the most probable classes that the NN indicated for that sample. For example, for a first picture (which has less than 1% porosity), the NN found that there is a 46% chance that it is part of the 0% porosity class, there is 44% chance that it is part of the 1% porosity class etc. This is a good estimate.

Each class is a range including the reference value (which may be the middle value of the range). For the results shown in FIGS. 5 and 6, the porosity range was split in the following classes: 0% class means porosity values from 0 to 0.5%, 1 class means porosity values between 0.5% and 1.5%, etc. As the amount of available training data increases, the ranges of porosity values spanned by the classes may be decreased, for example, down to 0.1%.

For most images, the trained NN performed well, but for some certain values (the lighter table cells) performance was average and occasionally it was considered unsatisfactory (the darker table cells). Training accuracy for the table in FIG. 5 was assessed to be 92%, cross entropy 0.505926 and validation accuracy 17%. However, instead of focusing on individual classes one should consider the overall classification result. In other words, the NN ability to correctly associate a porosity value to an image should be not be evaluated not through the perspective of a single class or image. If the first line of the table indicates the most likely class, it may be more relevant to combine the five lines together in a weighted average for an overall porosity estimation unbiased a certain class. For the first row in FIG. 5, the most likely class is 0%, but the porosity value calculated as a weighted average is 0.76%.

A third (production) phase is using the trained neural network to obtain predicted "log" porosity values based on cutting images associated with locations for which there are no wireline porosity values (e.g., in non-vertical wells). Cuttings 343 are prepared and analyzed with a SEM 340 to obtain unlabeled images 345. These images are input to the trained (or re-trained) neural network 322, which then outputs predicted "log" porosity values 347 corresponding to unlabeled images 345.

This new approach provides the advantage of reducing the difference between cutting-based porosity values and wireline logging-based porosity, which differences were caused by the different conditions (in-situ versus at surface), different type of measurements (logging versus image processing) and different sampling interval. Once the NN is trained, the current approach is faster and more reliable.

One challenge of the approach outlined in FIG. 3 is the lack of or a limited training dataset. Hundreds or thousands of images are needed for each porosity interval (known as a class), e.g., one class per porosity percent. The training dataset can be expanded by using image transformations such as rotation, reflection, etc., that can produce additional images usable for training in addition to the original image.

The assumption that the cuttings would yield the same image regardless of location (depth, basin, etc.) may be limiting in some circumstances. Another similar assumption may be related to the manner in which the well is drilled. Drill bit size, the drill's rate of penetration, and other drilling-related variables may also affect the cutting aspect. As the training database increases, it may be refined with additional parameters to overcome such potential limitations. The above-described approach may potentially be extended to estimate mineralogy and texture information and use the additional information to cross-validate the porosity estimates.

This approach may also be used when wireline porosity values are available but are unreliable being derived from uncalibrated density or neutron tools, not measured or cross-checked relative to direct measurements like on cores. Comparing the wireline porosity values with the ones predicted based on the cutting images can be used validate (or invalidate) the former ones.

Figure 7:
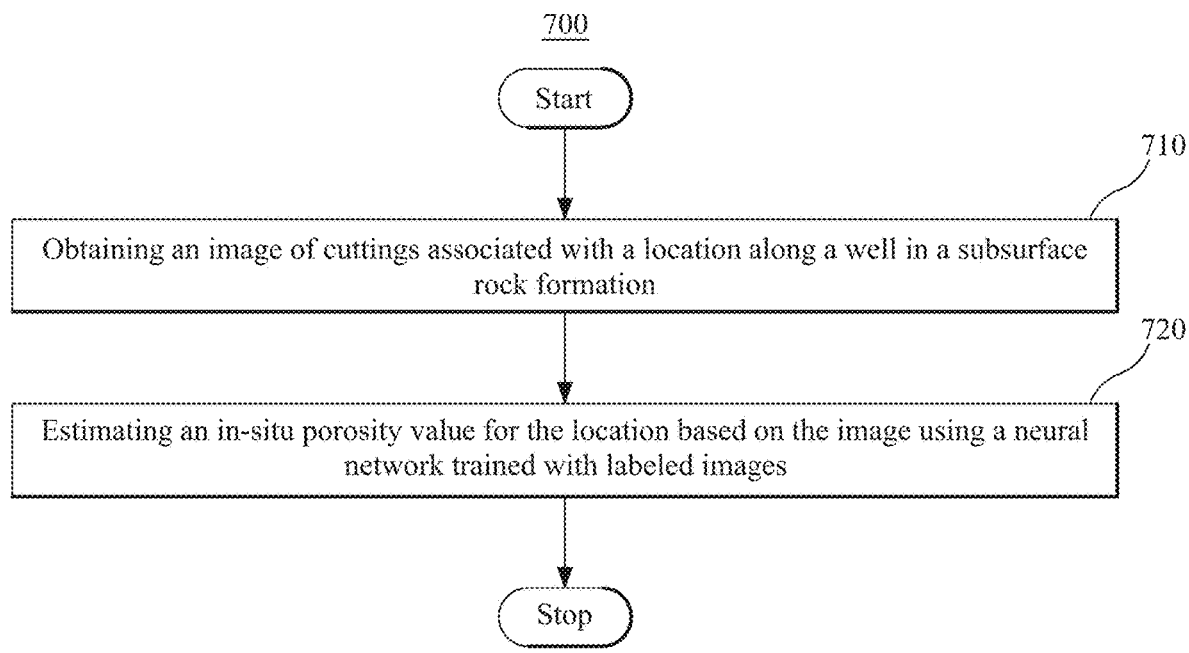
FIG. 7 is a flowchart of a method according to an embodiment.

A flowchart of a method 700 for estimating in-situ porosity according to an embodiment is illustrated in FIG. 7. At 710, an image of cuttings associated with a location along a well is obtained. At 720, a neural network estimates an in-situ porosity value based on the image. The neural network has been trained with labeled images, the labels indicating porosity values. Although method 700 is defined for a single image, it is usually used for plural locations, which may be at regular intervals along a well. The location (s) may be along a horizontal well.

The method may further include training the neural network using the labeled images. Each of the labeled images may be classified in a porosity class, each class spanning a predefined porosity value range including a reference class value.

The method may also include validating the neural network. Such validation (known as a blind test) may include (1) obtaining images of cuttings associated with corresponding wireline porosity values, (2) estimating porosity values for the images using the trained neural network, and (3) comparing the porosity values with the corresponding wireline porosity values. All images for which corresponding wireline porosity values are known are added to the training set (regardless whether the NN was able to predict correctly or not porosity before being included in the training set). Training and validating are ongoing processes as any extra data expanding the training dataset improves the overall predictive performance of the NN.

Figure 8:
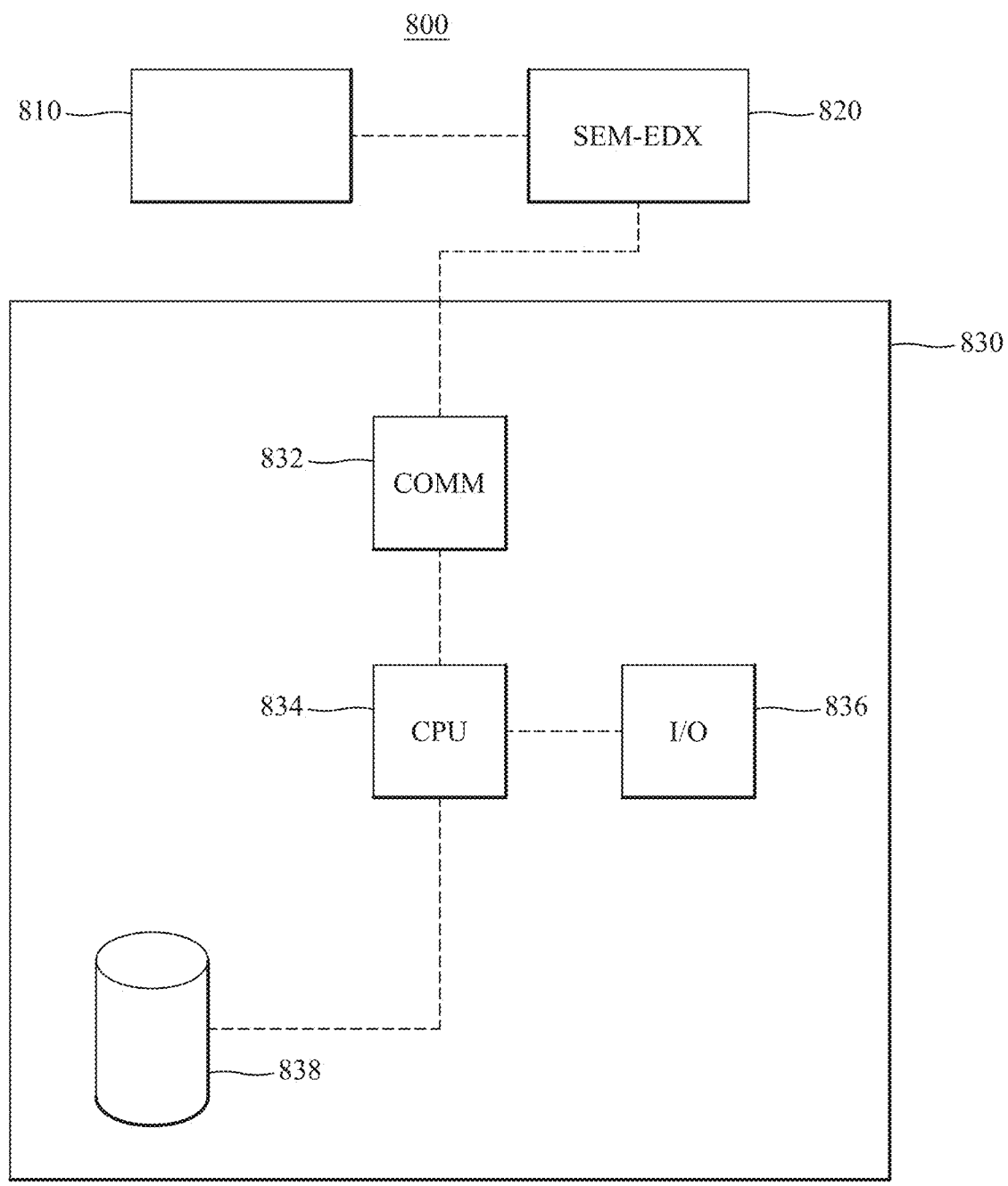
FIG. 8 is a block diagram of a system according to an embodiment.

FIG. 8 is a block diagram of a system 800 according to an embodiment. The system includes a sample preparation installation 810 for preparing cuttings from locations along the wellbore for a SEM analysis, a SEM 820 for analyzing the prepared cuttings from locations to estimate porosity values associated with the locations, and a data processing apparatus 830.

The data processing apparatus includes an interface 832 for receiving the images and a central processing unit 834 including at least one processor. The processor executes neural network software trained with labeled images, wherein labels of the labeled images indicate porosity values. The trained NN then receives as input one or more cutting images and outputs estimated in-situ porosity values.

Data processing apparatus 830 may also include a user interface 836 and a memory 838. The memory may store the neural network software that makes the central processing unit execute a method like the ones described in this document.

The disclosed embodiments provide methods and systems for estimating in-situ porosity based on cutting images. It should be understood that this description is not intended to limit the invention. On the contrary, the embodiments are intended to cover alternatives, modifications and equivalents, which are included in the spirit and scope of the invention as defined by the appended claims. Further, in the detailed description of the embodiments, numerous specific details are set forth in order to provide a comprehensive understanding of the claimed invention. However, one skilled in the art would understand that various embodiments may be practiced without such specific details.

Although the features and elements of the present embodiments are described in the embodiments in particular combinations, each feature or element can be used alone without the other features and elements of the embodiments or in various combinations with or without other features and elements disclosed herein.

This written description uses examples of the subject matter disclosed to enable any person skilled in the art to practice the same, including making and using any devices or systems and performing any incorporated methods. The patentable scope of the subject matter is defined by the claims, and may include other examples that occur to those skilled in the art. Such other examples are intended to be within the scope of the claims.

What is claimed is:

1. A method for estimating in-situ porosity based on cutting images, the method comprising:
    obtaining an image of cuttings associated with a location along a well in a subsurface rock formation; and
    estimating an in-situ porosity value for the location based on the image using a neural network trained with labeled images,
    wherein labels of the labeled images indicate porosity values, and
    the in-situ porosity value is usable to infer elastic and/or mechanical properties at the location.

2. The method of claim 1, wherein the obtaining and the estimating are performed for plural locations.

3. The method of claim 2, wherein the plural locations are at regular intervals along the well.

4. The method of claim 2, wherein the plural locations are along a horizontal portion of the well.

5. The method of claim 1, further comprising:
    training the neural network using the labeled images associated with porosity classes, each class spanning a predefined porosity value range including a reference class value.

6. The method of claim 1, further comprising validating the neural network by:
    obtaining images of cuttings not used to train the neural network, associated with corresponding wireline porosity values;
    estimating porosity values for the images using the trained neural network; and
    comparing the porosity values with the corresponding wireline porosity values.

7. The method of claim 6, wherein the validating further includes adding one or more of the validating images and respective wireline porosity values to the labeled images.

8. A system for estimating in-situ porosity based on cutting images, the system comprising:
    a data processing apparatus including
        an interface configured to receive an image of cuttings associated with a location along a well in a subsurface rock formation; and
        a central processing unit connected to the interface and configured to estimate an in-situ porosity value for the location based on the image using a neural network trained with labeled images,
    wherein labels of the labeled images indicate porosity values, and
    the in-situ porosity value is used to infer elastic and/or mechanical properties at the location.

9. The system of claim 8, further comprising:
    a sample preparation installation configured to preparing cuttings from the location for analysis.

10. The system of claim 8, further comprising:
    a scanning electron microscope configured to generate the image.

11. The system of claim 8, wherein the interface receives plural cutting images associated with plural locations and the central processing unit estimates plural corresponding in-situ porosity values.

12. The system of claim 11, wherein the plural locations are at regular intervals along the well.

13. The system of claim 11, wherein the plural locations are along a non-vertical portion of the well.

14. The system of claim 8, wherein the central processing unit is further configured to train the neural network using the labeled images associated with porosity classes, each class spanning a predefined porosity value range including a reference value.

15. The system of claim 8, wherein the central processing unit is further configured to validate the neural network by:
    obtaining validating images of cuttings associated with corresponding wireline porosity values;
    estimating porosity values for the validating images using the neural network; and
    comparing the porosity values with the corresponding wireline porosity values.

16. The system of claim 15, wherein the central processing unit is further configured to add one or more of the validating images and respective wireline porosity values to the labeled images.

17. A non-transitory computer readable recording media storing executable codes, which, when executed by a processor connected to an interface, make the processor
    to estimate an in-situ porosity value for a location along a well in a subsurface rock formation based on a cutting image received by the interface, using a neural network
    wherein the neural network has been trained with labeled images, labels of the labeled images indicating porosity values, and
    the in-situ porosity value is usable to infer elastic and/or mechanical properties at the location.

18. The non-transitory computer readable recording media of claim 17, wherein the executable codes further make the processor to train the neural network using the labeled images associated with porosity classes, each class spanning a predefined porosity value range including a reference value.

19. The non-transitory computer readable recording media of claim 17, wherein the executable codes further make the processor to validate the neural network by:
    obtaining validating images of cuttings associated with corresponding wireline porosity values;
    estimating porosity values for the validating images using the neural network; and
    comparing the porosity values with the corresponding wireline porosity values.

20. The non-transitory computer readable recording media of claim 18, wherein the executable codes further make the processor to select and add one or more of the validating images and respective wireline porosity values to the labeled images.

* * * * *